United States Patent [19]

Borland et al.

[11] Patent Number: 5,167,874
[45] Date of Patent: Dec. 1, 1992

[54] SURFACTANT MIXTURES

[75] Inventors: James E. Borland; Terry Crutcher; Joe D. Sauer; Kim R. Smith, all of Baton Rouge, La.

[73] Assignee: Ethyl Corporation, Richmond, Va.

[21] Appl. No.: 788,815

[22] Filed: Nov. 7, 1991

[51] Int. Cl.$^5$ .................................................. C11D 1/18
[52] U.S. Cl. ............................... 252/547; 252/558; 252/559; 252/DIG. 5; 252/DIG. 13; 252/DIG. 14
[58] Field of Search ......... 252/547, 558, 559, DIG. 5, 252/DIG. 13, DIG. 14

[56] References Cited

U.S. PATENT DOCUMENTS

| 3,609,075 | 9/1971 | Barbera | 257/174.16 |
| 4,784,777 | 11/1988 | Dellinger | 252/546 |
| 4,820,436 | 4/1989 | Andree et al. | 252/548 |
| 4,985,177 | 1/1991 | Tosaka et al. | 252/DIG. 14 |

Primary Examiner—Patrick P. Garvin
Assistant Examiner—E. D. Irzinski
Attorney, Agent, or Firm—Patricia J. Hogan

[57] ABSTRACT

Surfactant mixtures which provide denser foams than the individual components consist of 50-90% by weight of an amine oxide corresponding to the formula RR'R"NO in which R is a primary alkyl group containing 6-24 carbons and R' and R" are independently selected from methyl, ethyl, and 2-hydroxyethyl and 50-10% by weight of an alkylbenzenesulfonate surfactant. Preferred mixtures are those in which the amine oxide is N-tetradecyldimethylamine oxide and the alkylbenzenesulfonate surfactant is sodium dodecylbenzenesulfonate.

4 Claims, No Drawings

SURFACTANT MIXTURES

FIELD OF INVENTION

This invention relates to surfactant compositions and more particularly to such compositions which are mixtures of amine oxides and alkylbenzenesulfonates.

BACKGROUND

It is known that various surfactants have been found to be useful in cleaning compositions, such as shower gels, shampoos, and light duty detergents (e.g., dish detergents)—compositions in which good foam density is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of alkylbenzenesulfonates as the anionic surfactants in these compositions permits the attainment of desirable characteristics, including reasonably good foamability, the density of the foam produced by an alkylbenzenesulfonate system is rather low. It would be beneficial to find a way of increasing that foam density.

SUMMARY OF INVENTION

It has been found that a mixture of 50-90% by weight of an amine oxide corresponding to the formula RR'R"NO in which R is a primary alkyl group containing 6-24 carbons and R' and R" are independently selected from methyl, ethyl, and 2-hydroxyethyl and 50-10% by weight of an alkylbenzenesulfonate surfactant provides a denser foam than either component of the surfactant mixture.

DETAILED DESCRIPTION

Amine oxides which can be used in the practice of the invention are compounds corresponding to the formula RR'R"NO in which R is a primary alkyl group containing 6-24 carbons, preferably 10-18 carbons, and R' and R" are independently selected from methyl, ethyl, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

The alkylbenzenesulfonates which may be used in admixture with the amine oxides may be any of the alkylbenzenesulfonates commonly used as anionic surfactants. These surfactants are usually alkali metal or ammonium salts of alkylbenzenesulfonates in which the alkyl group contains 8-18 carbons. A particularly preferred alkylbenzenesulfonate surfactant is sodium dodecylbenzenesulfonate.

The amine oxide/alkylbenzenesulfonate mixtures of the invention are synergistic in all proportions and provide denser foams than can be achieved by the use of either component alone. Highest foam densities are obtained when the mixtures contain 65-80% by weight of the amine oxide.

The invention is advantageous in that it provides novel surfactant mixtures which can provide denser foams than the individual components of the mixtures. This characteristic of the mixtures makes them valuable for use in the cleaning compositions which require reasonably dense foam production for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Prepare several aqueous solutions having a total surfactant content of 5% from N-tetradecyldimethylamine oxide and sodium dodecylbenzenesulfonate. Test each solution to show the density of the foam it can produce by placing 25 mL of the solution in a 100 mL blender cup, mixing for 15 seconds, transferring the foam to a tared graduated cylinder, and calculating the foam density. The proportions of amine oxide and sulfonate used in preparing each of the solutions and the foam densities obtained from them are shown in the table below.

TABLE

| % Amine Oxide | % Sulfonate | Density (g/mL) |
| --- | --- | --- |
| 100 | 0 | 0.188 |
| 75 | 25 | 0.864 |
| 50 | 50 | 0.460 |
| 25 | 75 | 0.207 |
| 0 | 100 | 0.144 |

What is claimed is:

1. A surfactant mixture consisting of 50-90% by weight of an amine oxide corresponding to the formula RR'R"NO in which R is a primary alkyl group containing 6-24 carbons and R' and R" are independently selected from the group consisting of methyl, ethyl, and 2-hydroxyethyl and 50-10% by weight of an alkylbenzenesulfonate surfactant.

2. The surfactant mixture of claim 1 wherein R is a primary alkyl group containing 10-18 carbons, R' and R" are methyl, and the alkylbenzenesulfonate surfactant is an alkali metal or ammonium salt of an alkylbenzenesulfonate in which the alkyl group contains 8-18 carbons.

3. The surfactant mixture of claim 2 wherein the amine oxide is N-tetradecyldimethylamine oxide and the alkylbenzenesulfonate surfactant is sodium dodecylbenzenesulfonate.

4. The surfactant mixture of claim 1 containing about 65-80% by weight of the amine oxide.

* * * * *